United States Patent [19]
Purcell et al.

[11] Patent Number: 5,945,449
[45] Date of Patent: Aug. 31, 1999

[54] STERILE BICARBONATE CONCENTRATE

[75] Inventors: Larry Joseph Purcell, Toronto; Sheldon William Tobe, North York, both of Canada

[73] Assignee: Dialysis Solutions Inc., Toronto, Canada

[21] Appl. No.: 08/961,778

[22] Filed: Oct. 31, 1997

Related U.S. Application Data

[60] Provisional application No. 60/030,110, Nov. 1, 1996.

[51] Int. Cl.$^6$ .................... A01N 47/06; A61K 31/265
[52] U.S. Cl. ................ 514/512; 514/23; 514/557; 514/680; 514/681; 514/686; 424/661; 424/663; 424/679; 424/680; 424/681
[58] Field of Search ................... 514/680, 681, 514/686, 512, 23, 557; 424/661, 663, 679, 680, 681

[56] References Cited

U.S. PATENT DOCUMENTS 5,211,643  5/1993  Reinhardt et al. ............... 604/416

OTHER PUBLICATIONS

Davenport et al., Nephron 59:461–465, 1991.
Hutchison and R. Gokal, Kidney Intl, vol. 42, Suppl. 38:S–153–S–159, 1992.
Jenkins et al., ASAIO Transactions 36:M465–M466, 1990.
Kaye et al., Clinical Nephrology 31:132–138, 1989.
Kaye and D. Fisher, Clinical Nephrology 34:84–87, 1990.
Kaye, Clinical Nephrology 40:221–224, 1993.
Leblanc et al., Am. J. Kid. Dis. 26:910–917, 1995.
Leblanc et al., J. Am. Soc. Nephrol (Abstract) 6:497, 1995.
Leenen, Artificial Organs 8:411–417, 1984.
Olbricht et al. Blood Purification in Perspective: New Insights and Future Trends vol. II, 306–310, 1992.
Schambye et al., Peritoneal Dialysis Intl, 12:281–286, 1992.
Tam et al., Clinical Nephrology 30:79–85, 1988.
Van Bommel et al, Am. J. Nephrol. 15:192–200, 1995.
Van Bommel, Nephrol. Dial. Transplant. Editorial Comments 311–314, 1995.
Veech et al., Am. J. Med. 82:572–574, 1987.
Wong et al., J. Am. Soc. Nephrol (Abstract) 6:515, 1995.

*Primary Examiner*—Frederick Krass
*Attorney, Agent, or Firm*—Bereskin & Parr

[57] ABSTRACT

A sterile bicarbonate concentrate for use in the present invention relates to a sterile calcium-free bicarbonate concentrate for use in peritoneal dialysis, hemofiltration, cardiac bypass surgery and in electrolyte replacement therapy.

18 Claims, No Drawings

STERILE BICARBONATE CONCENTRATE

This application claims the benefit of U.S. Provisional Application Ser. No. 60/030,110, filed Nov. 1, 1996.

FIELD OF THE INVENTION

The present invention relates to a sterile calcium-free bicarbonate concentrate for use in peritoneal dialysis, hemofiltration, cardiac bypass surgery and in electrolyte replacement therapy.

BACKGROUND OF THE INVENTION

The purification of blood and separation of fluids using dialysis can be advantageously used in many medical applications, particularly conditions where renal function has significantly declined. Dialysis removes wastes from blood through a semipermeable membrane by diffusive or convective processes. There are two principal dialysis methods used to support patients requiring renal replacement therapy: hemodialysis and peritoneal dialysis Hemodialysis, involves the removal of solutes and fluids (such as urea, creatinine and uric acid) from the blood through a dialysis membrane by diffusion into a dialysate. The dialysis membrane is a semipermeable membrane which is typically made of cellulose. Blood solutes containing the waste permeate through the membrane and into a dialysis solution or dialysate formulated to control solute net movement through the membrane.

In the chronic hemodialysis setting, processes which have been developed and are commonly used provide bicarbonate dialysis using a highly sophisticated machine which can be monitored by a team. Dialysis provided in the intensive care setting for patients with an acute loss of kidney function has traditionally been provided with a chronic hemodialysis machine, brought into the unit and operated by one dialysis nurse per patient, in addition to the patient's intensive care nurse.

Hemodialysis can be either continuous or intermittent. Intermittent hemodialysis involves short intensive periods of treatment on alternate days, while continuous hemodialysis involves continuous fluid removal and continuous blood purification.

Peritoneal dialysis, which also uses reverse osmosis principles, is another procedure which is used to remove waste products from a patient. This type of dialysis uses the peritoneal lining of the patient's abdomen as a semipermeable membrane to filter blood. In peritoneal dialysis, peritoneal dialysate is infused into the patient's peritoneum through a catheter. Fluid and waste removal is achieved by an osmotic gradient from the blood to the dialysate, generated by a high glucose concentration, permitting water to flow out from the blood. Fluids and waste products pass from the many blood vessels and capillaries in the peritoneal membrane into the dialysate, and after a sufficient period of time the dialysate containing the fluids and waste products is drained from the abdomen.

Chronic peritoneal dialysis is most often performed by the patient alone in their home after suitable training in a dialysis center, and Involves the use of individually applied bags of ready made, sterile, lactate buffered dialysis solution.

Due to resource limitations dialysis often must be condensed into a period of hours and may be limited to less than daily treatments leading to large fluctuations in levels of the substances removed front the patient. These fluctuations may adversely affect patient outcomes. A dialysis therapy which comes closest to normal kidney function, by operating continuously may improve patient outcomes and shorten intensive care stays, This has led to the adoption of continuous modalities of renal replacement therapy (CRRT) in the intensive care setting.

Continuous renal replacement therapy (CRRT) is dialysis continued 24 hours a day. Unlike chronic haemodialysis there are no standardized equipment or processes for CRRT. To simplify the equipment necessary, CRRT does not use dialysate from concentrate, but uses pre-made dialysate, usually peritoneal dialysis solution. This solution is sterile and is buffered by lactate. The dialysis solution to which blood is exposed through this membrane should have the same electrolyte composition of normal serum or it may induce fatal electrolyte abnormalities. Its use with dialysis filters requires at a minimum the absence of pyrogens. If the solution is to be given intraperitoneally or intravenously it must be sterile and pyrogen free.

The electrolyte composition of all dialysis solutions may vary but in a narrow range. The major cationic electrolyte component is sodium, usually at the concentration it is found in serum 140 (mmol/L, mEq/L). Other cations include calcium (2.5 mmol/L, 5.0 mEq/L, 10 mg/dl) and magnesium (0.75 mmol/L, 1.5 mEq/L,×mg/dl). The major anion is chloride whose concentration is determined by the net of the cationic charge constituents less the anionic buffer. The dialysis solutions used in all forms of dialysis contain buffers in an attempt to correct metabolic acidosis. Common buffers used include bicarbonate, lactate and acetate buffers.

Bicarbonate buffer is a preferred buffer for dialysis since bicarbonate is the physiological buffer of the body. However, pre-made mixtures of bicarbonate buffered solutions are difficult to sterilize and store because released carbonate will precipitate with calcium if present. Attempts have been made to stabilize calcium, for example with glycylglycine (U.S. Pat. No. 5,211,643 to Reinhardt et al). Continuous dialysis against an agent such as glycylglycine produces levels in the blood close to those present in the dialysate. The effect of long term exposure to stabilizing agents such as glycylglycine is unknown (Yatzidis et al. Nephron., 64:27–31, 1993).

Furthermore, sugars in a dialysis solution will caramelize during heat sterilization and prolonged exposure if kept at neutral or higher pH (7.4). Therefore sugar containing dialysis solution is kept at low pH. For example, pH 5.4 for most peritoneal dialysis solutions. The low pH is believed to be the source of pain patients suffer after instillation of a fresh bag of peritoneal dialysis solution. Low pH solutions are known to reduce the effectiveness of peritoneal immnunologic defences. The safety of using low pH solutions for dialysis or hemofiltration during CRRT has not been studied.

Also, during preparation and storage of a bicarbonate buffered solution, $CO_2$ is released from the solution, changing the bicarbonate concentration and pH of the solution. It is therefore necessary for bicarbonate containing solutions to be stored in glass or $CO_2$ impermeable plastic containers. The following solutions have been proposed to control the $CO_2$ content of the bicarbonate solution for peritoneal dialysis: storage in a powder form until use; use of an impermeable barrier between calcium containing and bicarbonate containing portions; and addition of buffers such as histidine or glycylglycine (H. Yatzidis, Nephron 64:27–31, 1993).

Dialysis care has become process driven to maximize the quality of the dialysis and to minimize costs. Hemodialysis machines have been developed which can prepare dialysis solution online from a single concentrate and clean water provided from a central reverse osmosis system. To get around the stability problems associated with calcium and bicarbonate, acetate was substituted for bicarbonate. Acetate hemodialysis was carried out until evidence showed the deleterious effects of acetate on dialysis patients, particularly with the use of the newer more biocompatible dialysis membranes (F. H. Leenen, Artificial Organs 8:411–417, November 1994).

Dual proportioning dialysis machines have been developed and employed at great expense to provide bicarbonate dialysis. These machines solve the calcium bicarbonate instability problem by keeping the bicarbonate and acid concentrates separate until the time of dialysis. Although micro precipitation may occur immediately after mixture, clinically this is not a concern even over a 72 hour period (Leblanc et al, 1995). However, because of this precipitation bicarbonate dialysis machines must have acid rinses on a regular basis. Separate batches of concentrates have been used using split bags which contain calcium and magnesium on the one hand, and the bicarbonate on the other hand to prevent precipitation (U.S. Pat. No. 4,630,727 to Feriani et al).

A method was been developed to allow an older single proportioning chronic dialysis machine to produce bicarbonate dialysis from concentrate using calcium free bicarbonate concentrate adding the calcium back into the blood by an infusion pump. This method for chronic dialysis was reported by Kaye et al, but was not adopted outside of Kaye's unit in Montreal. (M. Kaye et al., Clinical Nephrology 31:132–138 1989; M. Kaye and D. Fisher, Clinical Nephrology 34:84–87, 1990; and M. Kaye, Clinical Nephrology 40:221–224, 1993). Calcium is infused distal to the dialyzer into the drip chamber using an infusion pump and is a component of the dialysate. In Kaye's studies, the patient's are not critically ill and his system is set up for chronic hemodialysis, not for acute hemodialysis. The concentrate used by Kaye is not sterile. Furthermore, Kaye's system is used for intermittent, but not for continuous dialysis.

Acute renal failure in critically ill patients, which is generally accompanied by metabolic derangements and high overall mortality, poses significant challenges for renal replacement therapy. Acute intermittent hemodialysis has been the conventional therapy. Bicarbonate dialysate which is typically used in acute intermittent hemodialysis is not sterile but only clean.

Problems with the rapid removal of fluid and changes in electrolytes which occur during high efficiency short term intermittent hemodialysis have led to the development and use of continuous renal replacement therapies (CRRT) for critically ill patients (P. Y. W. Tam et al., Clinical Nephrology 30:79–85, 1988 and E. F. H. Van Bommel et al, Am. J. Nephrol. 15:192–200, 1995). Solute and volume removal are slow and continuous during CRRT eliminating the large shifts occurring between body compartments during intermittent hemodialysis, which may lead to hypotension and interfere with renal recovery (E. F. H. Van Bommel, Nephrol. Dial. Transplant. 1995 Editorial Comments, p. 311). CRRT techniques include peritoneal dialysis, continuous arterio-venous and veno-venous ultrafiltration, hemofiltration, hemodialysis and heimodiafiltration. Traditionally CRRT has used peritoneal dialysis solution as the dialysate and infusate.

Lactate containing peritoneal dialysis solution has been used in CRRT dialysate with some success (Baxter and Gambro solutions). Lactate is stable with calcium and is stable at low pH (5.4). Lactate is metatbolised by the intact functioning liver into bicarbonate, the body's natural buffer. However, lactate infusions are known to induce panic in susceptible individuals and may alter metabolism to favour catabolism over anabolism (R. L. Veech et al.). Its safety in CRRT dialysis has not been tested. However, its use as a buffer in peritoneal dialysis solution is universal and appears to be tolerated, except for abdominal pain and possible immunologic effects; there is mounting evidence that exposure to large amounts of lactate, particularly in the racemic form, may not be benign. Lactate included in these solutions is of the racemic form.

In intensive care patients, such as patients who have developed hypotension and lactic acidosis, lactate from the dialysis solution may not be metabolized to bicarbonate because of liver dysfunction, and when the dialysate lacks bicarbonate, acidosis may be worsened due to bicarbonate removal during dialysis. (A. Davenport et al., Nephron 1991:59:461–465, 1991 and M. Leblanc et al., Am. J. Kid. Dis. 26:910–917, 1995). For acute hemodialysis in the intensive care unit CRRT typically uses lactate based sterile solutions as dialysate and infusate (peritoneal dialysis solution). Research into methods to provide bicarbonate dialysate have been ongoing, Recently, a method was reported for providing non-sterile calcium bicarbonate dialysate for patients in the intensive care undergoing CRRT (M. Leblanc, AJKD 26(6):910–917, 1995). Non-sterile bicarbonate dialysis solutions can be produced in the chronic hemodialysis unit and carried to the intensive care unit. These methods are labour intensive, unregulated, non sterile, not pyrogen free, expensive and may lack sufficient quality control. Unlike chronic hemo- or peritoneal dialysis, which are process driven and carried out in a uniform, cost effective quality controlled manner, CRRT is carried out in many different modalities specific to each intensive care unit.

It is important to use a sterile dialysis solution in CRRT in order to avoid pyrogenic reactions caused by bacteria and endotoxin contamination of the dialysate solution. It is also important to have a solution which is readily available for use. While sterile lactate or acetate-based dialysis solutions may be used in CRRT they suffer from the disadvantages discussed above. It has been suggested that bicarbonate dialysate may be preferable to lactate or acetate-based solutions (M. Leblanc et al., Am. J. Kid. Dis, 26:910–917, 1995). However, it has not been possible to provide a sterile and readily available bicarbonate solution for CRRT due to the problems discussed above with bicarbonate solutions.

SUMMARY OF THE INVENTION

Broadly stated, the present invention provides a sterile calcium-free bicarbonate concentrate comprising sodium chloride (NaCl) 86.87±8.6 g/l, magnesium chloride ($MgCl_2$) 2.05±0.2 g/l, and sodium bicarbonate ($NaHCO_3$) 39.69±3.9 g/l. The concentrate can be stored at room temperature for up to 48 months. The concentrate may also contain potassium, dextrose and/or β-hydroxy-butyrate or other ketones.

The invention also relates to a sterile solution comprising the bicarbonate concentrate of the invention and a physiologically acceptable diluent. The sterile solution comprises Na 140±14 mmol/l, Mg 0.75±0.07 mmol/l, Cl 106.5 10 mmol/l, and $HCO_3$ 35.0±3.5 mmol/l.

The inventors have determined that the concentrate and sterile solutions of the concentrate can be used in a number of novel applications including (1) as a dialysate in (a) peritoneal dialysis, (b) hemodialysis of critically ill patients and (c) in cardiopulmonary bypass surgery; (2) as an infusate for hemofiltration; and (3) as an oral electrolyte fluid replacement.

The concentrate of the invention can be used to prepare ready made sterile solutions such as dialysates for peritoneal dialysis, infusates for general IV solutions, and oral electrolyte replacement solutions. The concentrate offers a convenient means to prepare sterile and pyrogen free solutions at the bedside. The bicarbonate concentrate of the invention may be provided as a sterile concentrate in unit dosage to be added to a fixed volume of sterile water in PVC bags or as a prediluted sterile solution containing Na 140±14 mmol/l, Mg 0.75±0.07 mmol/l, Cl 106.5±10 mmol/l, and $HCO_3$ 35.0±3.5 mmol/l. The concentrate and the dilute solution contained in glass or $CO_2$ impermeable plastic bags are stable and able to be stored for prolonged periods (up to 2 years.).

DETAILED DESCRIPTION OF THE INVENTION

The present inventors have developed a sterile calcium-free bicarbonate concentrate containing magnesium, sodium, chloride and bicarbonate that can be used in a number of novel applications. In one aspect, the present invention provides a sterile calcium-free bicarbonate concentrate comprising sodium chloride (NaCl) 86.87±8.6 g/l, magnesium chloride ($MgCl_2$) 2.05±0.2 g/l, and sodium bicarbonate ($NaHCO_3$) 39.69±3.9 g/l. The concentrate may also contain potassium, dextrose and/or ketones such as β hydroxy-butyrate. The concentrate can be stored at room temperature for up to 48 months.

In a preferred embodiment, the concentrate consists essentially of sodium chloride (NaCl) 86.87±8.6 g/l, magnesium chloride ($MgCl_2$) 2.05±0.2 g/l, and sodium bicarbonate ($NaHCO_3$) 39.69±3.9 g/l.

In one embodiment, the concentrate may be used in continuous renal replacement therapies (CRRT) such as peritoneal dialysis and hemofiltration. The concentrate can be diluted in sterile physiologically acceptable diluents and used as a dialysis solution. The dialysis solution of the invention which provides a more physiological dialysis solution when compared to lactate dialysis solutions containing glucose and lactate and/or calcium. The bicarbonate concentrate of the present invention provides a dialysis solution that avoids the problems of prior art bicarbonate dialysis solutions in that it is highly stable i.e. calcium does not precipitate, and the concentrate can be stored for about up to 24 months. Preferably the dialysis solution is used for acute hemodialysis in intensive care patients.

The bicarbonate concentrate and dialysis solution of the invention are cost effective because they facilitate process changes that increases efficiency by simplifying patient management, thus reducing nursing and medical staff time. They reduce or eliminate the need for corrective measures due to lactate or dextrose contained in other dialysates, lowering costs of extra syringes, needles, insulin, bicarbonate, etc. They also replace problematic lactate based peritoneal dialysis solutions used for dialysate in continuous hemodialysis all of which lead to a shorter number of days required in the intensive care unit (ICU).

It has been found that the bicarbonate concentrate of the present invention and dialysis solutions prepared from the concentrate are very suitable for CRRT, and in particular in CRRT adapted for acute renal replacement therapy of critically ill patients in particular, patients in intensive care units. The stability and sterility of the dialysis concentrate of the invention necessarily results in reduced renal replacement therapy costs.

The bicarbonate concentrate may be prepared by mixing the various components of the concentrate using conventional methods. The bicarbonate concentrate of the invention may be prepared according to the constituent ranges, or according to the preferred amounts set forth herein to prepare a unit dose i.e. a dose amount that can be mixed with a predetermined amount of a sterile physiologically acceptable diluent (e.g. 1, 3 or 5 litres of sterile water) to prepare a dialysis solution.

The bicarbonate concentrate may be used to produce a dialysis solution by mixing a sterile physiologically acceptable diluent with the concentrate. Accordingly, in another aspect the invention provides a dialysis solution comprising the bicarbonate concentrate of the invention and a physiologically acceptable diluent. Physiologically acceptable diluents which may be used in the dialysis solution of the invention include sterile water and dextrose 5% in water (for injection).

The bicarbonate solution is generally prepared by mixing 80±1 ml, preferably 80 ml of concentrate, with 1 litre of a sterile physiologically acceptable diluent. In an embodiment of the invention the dialysis solution may be prepared pre-diluted and stored in $C0_2$ impermeable bags. It consists of the following in mmol per litre: Na 140±14 mmol/l, Mg 0.75±0.07 mmol/l, Cl 106.5±10 mmol/l, and HCO3 35.0±3.5 mmol/l. The dialysis solution may contain potassium, up to 4 mmol/litre, and/or β hydroxy-butyrate or other ketones, up to 5 mmol/litre. Preferably, the dialysis solution consists of the following in mmol per litre: Na 140, Mg 0.75, Cl 106.5, and HCO3 35.0. If the dialysis solution is made in a PVC (polyvinyl chloride type) plastic container, it is advisable to use it within about 72 hours in order to avoid loss of bicarbonate through the plastic. The dialysis solution may be stored at room temperature or refrigerated. Calcium may be added to the diluent for CRRT, just prior to administration (M Leblanc et al, AJKD, 1995).

In a further aspect, the present invention provides a method for providing continuous renal replacement therapy to a patient comprising administering a sterile dialysis solution comprising Na 140±14 mmol/l, Mg 0.75±0.07 mmol/l, Cl 106.5±10 mmol/l, and HCO3 35.0±3.5 mmol/l to a patient in need thereof. The present invention also provides a use of a concentrate comprising sodium chloride (NaCl) 86.87±8.6 g/l, magnesium chloride ($MgCl_2$) 2.05±0.2 g/l, and sodium bicarbonate ($NaHCO_3$) 39.69±3.9 g/l for preparing a dialysis solution for use in continuous renal replacement therapy.

The dialysis solution of the invention is preferably used to treat acute renal failure in critically ill patients. In contrast to prior art dialysis methods, the treatment typically does not involve incorporating calcium into the blood using the dialysis procedure. Therefore, the invention also contemplates a method for treating acute renal failure in a critically ill patient comprising dialyzing blood from the patient without introducing calcium into the blood removed from the patient during dialysis, and using a sterile dialysis solution prepared by mixing a sterile diluent with a sterile bicarbonate concentrate comprising NaCl 86.87±8.6 g/l, $MgCl_2$ 2.05±0.2 g/l, and $NaHCO_3$ 39.69±3.9 g/l. The dialysis solution may additionally contain potassium, up to 4 mmol/litre, glucose up to 5 mmol/litre and/or β hydroxy-butyrate or other ketones, up to 5 mmol/litre.

The term "critically ill patient" or "critically ill patients" refers to patients that have a high mortality rate, acute renal failure, multiple organ failure, and multiple metabolic derangements. Critically ill patients which can be treated using the dialysis solution of the invention typically have acute renal failure and a high APACHE II score (Knaus W.A. Et al., Crit. Care Med. 13:818–827, 1985). An assessment of the number of failing organs may be performed using the procedure described in Jordan, D.A. Et al., Crit Care Med 15:897–904, 1987.

The bicarbonate concentrate and dialysis solution of the invention are preferably administered to patients in intensive care who require dialysis and are hemodynamically unstable, or whose liver function is either impaired or at risk of impairment. Liver transplantation patients are especially difficult to manage and very often cannot handle any dialysate which contains lactate. Unable to transform the lactate in lactate buffered dialysis solutions to bicarbonate, they will go into acidosis if such solutions are used, and they require large doses of bicarbonate to correct pH imbalance. Many of these patients are also unable to handle the dextrose delivered by usual dialysates and may therefore require insulin to correct hyperglycemia which may extend stay in the intensive care unit and add to costs.

The dialysis solution of the invention is compatible with all systems used for CRRT including the commercially available systems such as the COBE Prisma Denver, Colo., Baxter CRRT System, Chicago, Ill., Hospital BSM22, Medolla, Italy, IMED Pump System, San Diego, Calif., Fresenius CRRT system, Dusseldorf, Germany or any other CRRT machine that uses peritoneal dialysate or other lactate-containing fluid or other bicarbonate based solutions as CRRT hemodialysate or infusate. When the dialysis solution is used with conventional systems for CRRT the consumption rate will typically be a unit dose of concentrate per hour assuming a dialysate flow of 1 litre per hour up to 2 litre per hour and a further 500 cc per hour of infusate.

In one embodiment, the bicarbonate concentrate and dialysis solution of the invention may be used for peritoneal dialysis. Consequently, the present invention provides a use of a sterile calcium free bicarbonate concentrate for preparing a dialysis solution for use in peritoneal dialysis, wherein said concentrate comprises sodium chloride (NaCl) 86.87±8.6 g/l, magnesium chloride (MgCl$_2$) 2.05±0.2 g/l, and sodium bicarbonate NaHCO$_3$) 39.69±3.9 g/l. The present invention also provides a method for providing peritoneal dialysis to a patient comprising administering a sterile dialysis solution comprising Na 140±14 mmol/l, Mg 0.75±0.07 mmol/l, Cl 106.5±10 mmol/l, and HCO3 35.0±3.5 mmol/l to a patient in need thereof.

In this embodiment, calcium should be added to the dialysate of the invention prior to administration to the patient. This may be accomplished by adding calcium to each liter of the dialysis solution. Calcium may be added to produce a final calcium concentration according to local protocol.

To produce a final calcium concentration in the range 1.25–1.75 mmol/L (5.0–7.0 mg/dl) calcium chloride 10% solution (100mg/ml, 1.4mEq/ml) 1.8–2.5 ml is added per 1080 ml of dialysate. Alternatively calcium gluconate 10% solution (100 mg/dl, 0.465 mEq/ml) 5.4–7.6 ml may be added per 1080 ml of dialysate to produce the same final calcium concentrations 1.25–1.75 mmol/L (5.0–7.0 mg/dL). Calcium may be added aseptically using a syringe and needle, either pre-loaded or else drawn from a multidose vial or through the use of a split bag system containing the calcium in a separate container which is then added to the solution prior to patient administration. In such a split bag system the dialysate is in a prediluted state.

As an example, the dialysis solution for peritoneal dialysis may be prepared as follows. To make two liters of dialysis solution, 160 ml of concentrate is added to a 2 litre bag of sterile water with calcium as above (to make a final volume of 2160 ml not including the calcium volume). The concentrate may either be added from a separate glass container or part of a split bag containing sterile water concentrate and calcium. Alternatively the bag may contain the dilute form of the dialysate (Na 140±14 mmol/l, Mg 0.75±0.07 mmol/l, Cl 106.5±10 mmol/l, and HCO$_3$ 35.0±3.5 mmol/l). The bicarbonate concentrate containing portion of the bag must be of appropriate carbon dioxide containing material (for example Stedim, San Diego). Final calcium concentrations for the peritoneal dialysis solution include the range of 1.25 to 1.75 mmol/L concentration. Such split bags may include a range of volumes from 2 liters to 10 liters with the previously described proportions of concentrate, water and calcium. A further embodiment of this solution for peritoneal dialysis may include β-hydroxy-butyrate or other ketones up to and including 5 mmol/L (51.8 mg/dL).

The ability to make sterile bicarbonate buffered peritoneal dialysate at the bedside is particularly advantageous in third world settings, where the technology and infrastructure for running hemodialysis may not be widely available. An example of a bedside set up in peritoneal dialysis includes a 2 liter plastic intravenous bag with connections to 1 liter of D5W (5% w/v dextrose in water) and 1 liter of sterile water. The 2 liter bag is prefilled with calcium 1.25–1.75 mmol/L (5.0–7.0 mg/dl) as calcium gluconate or chloride as above. The addition of 1000 ml of sterile water, 160 ml of concentrate and 1000 ml of D5W produces a solution of the following concentrations Na 140±14mmol/l, Mg 0.75±0.07 mmol/l, Cl 106.5±10 mmol/l, and HCO$_3$ 35.0±3.5 mmol/l and dextrose 2.5% w/v. In another example, a peritoneal dialysis solution containing 2.5% dextrose can be produced by mixing 1 litre of D5W, 1 litre of sterile water and 160 ml of the bicarbonate concentrate and CaCl.

The present invention includes kits for preparing dialysis solutions. In one embodiment, the present invention provides a kit for preparing a dialysis solution comprising (a) one 80 ml unit of a concentrate comprising sodium chloride (NaCl) 86.87±8.6 g/l magnesium chloride (MgCl$_2$) 2.05±0.2 g/l, and sodium bicarbonate NaHCO$_3$) 39.69±3.9 g/l and (b) one litre of sterile water. In another embodiment, the present intention provides a kit for preparing a dialysis solution comprising (a) two 80 ml units of a concentrate, each unit comprising sodium chloride (NaCl) 86.87±8.6 g/l, magnesium chloride (MgCl$_2$) 2.05±0.2 g/l, and sodium bicarbonate NaHCO$_3$) 39.69±3.9 g/l (b) one litre of sterile water and (c) one litre of a 5% w/v dextrose solution in water. The kits of the invention may optionally include a calcium solution to bring the final calcium concentration in the dialysis solution to about 1.25–1.75 mmol/L.

The bicarbonate concentrate and dialysis solution of the invention may also be used for slow nocturnal hemodialysis. This is a form of dialysis where patients dialyse themselves at home overnight using a modified hemodialysis machine. In this embodiment, the concentrate would be added to clean water prepared for hemodialysis by water purification such as reverse osmosis or deionizatioon as appropriate for local water supply. 80 ml of bicarbonate concentrate is added to each liter of clean water to make 1080 ml dialysate. In this embodiment, calcium must be added to the dialysate of the invention prior to administration to the patient. This may be accomplished by adding calcium to each liter of the dialysis solution. Calcium may be added to produce a final calcium concentration according to local protocol. To produce a final calcium concentration in the range 1.25–1.75 mmol/L (5.0–7.0 mg/dL) calcium chloride 10% solution (100 mg/ml, 1.4 mEq/ml) 1.8–2.5 ml is added per 1080 ml of dialysate. Alternatively calcium gluconate 10% solution (100 mg/dl, 0.465 mEq/ml) 5.4–7.6 ml may be added per 1080 ml of dialysate to produce the same final calcium concentrations 1.25–1.75 mmol/L (5.0–7.0 mg/dl). Calcium may be added aseptically using a syringe and needle or through the use of a split bag system containing the calcium in a separate container which is then added to the solution prior to patient administration.

The dialysis solution of the invention, either the concentrate or the diluted solution, may be contained in a plastic container (bag) for use at the bedside.

In a preferred embodiment, the solution will be prepared to a desired concentration for dialysis; Na 140±14 mmol/l, Mg 0.75±0.07 mmol/l, Cl 106.5±10 mmol/l, and $HCO_3$ 35.0±3.5 mmol/l. In this embodiment, sterile water and all electrolytes, except calcium, are mixed, and if desired, diluted, and placed in a bag impermeable to carbon dioxide. At the time of dialysis, calcium may be added from, for example, a pre-filled syringe. Calcium may be added to produce a final calcium concentration according to local protocol. To produce a final calcium concentration in the range 1.25–1.75 mmol/L (5.0–7.0 mg/dl) calcium chloride 10% solution (100 mg/ml, 1.4 mEq/ml) 1.8–2.5 ml is added per 1080 ml of dialysate. Alternatively calcium gluconate 10% solution (100 mg/dl, 0.465 mEq/ml) 5.4–7.6 ml may be added per 1080 ml of dialysate to produce the same final calcium concentrations 1.25–1.75 mmol/L (5.0–7.0 mg/dL).

In one embodiment of the invention, the pre-filled syringe with calcium is sold in a kit form with the bag. In another, a section of the bag will be sealed off and filled with a calcium solution. When required, the separating mechanism membranes within the bags will be broken, and calcium will be released into the portion bag containing the sterile water and the other electrolytes. In one embodiment the calcium will be injected by pre-attached syringe to the spike attachment port of the bag. After injection the syringe is broken away revealing the spike site. This allows for aseptic spiking and a failsafe device to prevent spiking of the bag without first injecting calcium. This would be the preferred embodiment for use in peritoneal dialysis where calcium inclusion is essential.

Containers, such as bags, which are impermeable to carbon dioxide are selected for use in the present invention. For example, a bag may be made with three layers of plastic material, sandwiched together (see for example, bag produced by Bieffe Medital, 20157 Milano, 41100 Modena, Italy, Stedim San Diego, Advanced Scientifics Pa.)

The bicarbonate concentrate and dialysis solution of the invention may also be used in patients undergoing cardiopulmonary bypass surgery. Accordingly, the present invention provides a use of a sterile calcium free bicarbonate concentrate for preparing a dialysis solution for use in cardiac bypass surgery, wherein said concentrate comprises sodium chloride (NaCl) 86.87±8.6 g/l, magnesium chloride ($MgCl_2$) 2.05±0.2 g/l, and sodium bicarbonate ($NaHCO_3$) 39.69±3.9 g/l.

Cardiac surgery requires a still, bloodless operating field which is generally achieved by inducing electromechanical arrest of the heart. A chemical solution (cardioplegia) is administered to the heart to produce cardiac arrest. Cardioplegia contains a number of components including potassium, and glucose. The administration of potassium cardioplegia produces unwanted problems in two clinical scenarios. In patients with oliguric renal failure the kidneys are not able to excrete the potassium load resulting in significant hyperkalemia. Continuous cardioplegia where the patient receives large volumes of cardioplegia, also produces significant hyperkalemia, hyperglycemia and dilutional hyponatremia. In these clinical scenarios hemodialysis with the dialysis concentrate and dialysis solution of the invention can be used to more effectively clear potassium from the circulation and reduce excess volume of fluid.

Consequently, in another aspect the present invention provides a method of reducing potassium levels and fluid volume during cardiopulmonary bypass surgery comprising administering a sterile dialysis solution comprising Na 140±14 mmol/l, Mg 0.75±0.07 mmol/l, Cl 106.5±10 mmol/l, and HCO3 35.0±3.5 mmol/l to a patient in need thereof.

In a further embodiment of the invention, the concentrate may be used as an infusate in hemodialysis. Consequently, the present invention provides a use of a sterile calcium-free bicarbonate concentrate for preparing an infusate for hemofiltration, wherein said concentrate comprises sodium chloride (NaCl) 86.87±8.6 g/l, magnesium chloride ($MgCl_2$) 2.05±0.2 g/l, and sodium bicarbonate ($NaHCO_3$) 39.69±3.9 g/l. The present invention also provides a method for hemofiltration comprising administering a sterile dialysis solution comprising Na 140±14 mmol/l, Mg 0.75±0.07 mmol/l, Cl 106.5±10 mmol/l, and HCO3 35.0±3.5 mmol/l to a patient in need thereof. The infusate may be prepared by mixing 1000 ml of sterile water to 80 ml of the bicarbonate concentrate. The infusate can be prepared when needed or can be prepared and stored in a suitable container, such as a bag, which is impermeable to carbon dioxide, until it is needed.

In another embodiment, the dialysis concentrate may be used as a sterile oral electrolyte solution for fluid replacement for example in treating dysentery. Consequently, the present invention provides a use of a sterile, calcium-free bicarbonate concentrate for preparing a solution for use in oral replacement therapy, wherein said concentrate comprises sodium chloride (NaCl) 86.87±8.6 g/l, magnesium chloride ($MgCl_2$) 2.05±0.2 g/l, and sodium bicarbonate ($NaHCO_3$) 39.69±3.9 g/l. The present invention also provides a method of treating dysentery comprising administering a solution comprising 90 mMol/l sodium; 68.5 mMol/l chloride; 22 mMol/l bicarbonate; and 277 mMol/l glucose to a person in need thereof.

In one embodiment, 50 ml of the concentrate is added to 1000 ml of 5% w/v Dextrose in water (D5W) to make a sterile solution of final concentration (Na 90, Cl 68.5, $HCO_3$ 22 Mg 0.5 and Glucose 277 mmol/L), which is close to the World Health Organization (WHO) oral rehydration solution. The drawbacks with the WHO solution is that it is generally diluted with the local water supply which is usually safe for consumption. In contrast, the concentrate of the present invention is diluted in a sterile D5W solution. In one embodiment, potassium supplements such as orange juice or coconut water may also be given. It may be used as an intravenous replacement solution for volume repletion in patients with cholera induced dysentery (80 ml into 1 liter of sterile water). In this embodiment, oral potassium must also be given as stool potassium loses exceed safe non-cardiac monitored intravenously administered potassium rates.

The amounts and components of the bicarbonate concentrate and dialysis solution of the invention may be modified to adapt to their use in cardiovascular surgery, peritoneal dialysis, hemodiafiltration, hemofiltration, and as an electrolyte solution.

The following non-limiting examples are illustrative of the present invention.

EXAMPLES

Example 1

Patients dialysed with the solution of the invention during bypass surgery

During bypass surgery, six patients were dialysed using the dialysis solution of the invention. After dilution, the dialysate solution contained approximately 140 mMol/l of Na, 0.75 mMol/l of Mg, 106.5 mMol/l of Cl, 35 mMol/l of $HCO_3$. Thirty other patients were dialysed using 1.5% Dianeal, a commercially available lactate based dialysate. The study found a 49% difference in glucose levels. In the six patients dialysed with the dialysate of the invention, glucose levels fell during dialysis from 14.6 mmol/L pre dialysis to 12.1 mmol/L post dialysis. In the thirty patients dialysed against the dianeal, glucose levels actually increased from 17.3 mmol/L pre-dialysis 18.8 mmol/L post dialysis. Higher glucose levels may be in part responsible for neurolgic deficits found post-bypass, and therefore an effort is being made to reduce hyperglycemia post-bypass, particularly in diabetic patients with poor kidney function, who are more likely to require dialysis as they come off the bypass pump. Bicarbonate levels rose in the 6 patients dialysed against the bicarbonate dialysate (22.5 to 23.5 mmol/L pre to post dialysis) while in the 24 patients dialysed against the lactate buffered dialysate (dianeal) bicarbonate levels fell from 23.5 to 21.8 mmol/L pre to post dialysis. Potassium levels were reduced to the same extent by both solutions.

Example 2

Case studies of patients treated with solutions of the invention a) The dialysate described in Example 1 was used on a patient who had liver failure and developed high lactate levels on lactate containing dialysis solution. The dialysate was delivered at 1 l/hr with Gambro AK10 (Gambro inc., Lundia, Sweden), and also used as replacement fluid at 500 ml/hr. On the bicarbonate dialysate of the invention the patient's acid base status normalized and he tolerated both the dialysis fluid and the infusion for over 36 hours, at which time dialysis was safely discontinued.

b) The dialysate described in example was used at 1 L/hr as dialysate with the Prisma continuous renal replacement therapy system, (Hospal Gambro inc. Lundia Sweden), A 46 year old male, a known ethanol abuser with a history of peptic ulcer disease and upper GI bleeding was admitted with a diagnosis of cirrhosis, hepatic encephalopathy and pneumonia as well as acute renal failure. He was initially treated with peritoneal dialysis via an acute peritoneal dialysis catheter but he remained under dialyzed and was switched to continuous veno venous hemo dialysis using the Prisma. The dialysate as described in Example 1 was used at a flow of 1 liter per hour and as a replacement IV solution at 1 liter per hour. It was prepared by adding 80 ml of concentrate aseptically to 1000 ml of sterile water in PVC bag (Baxter Health Care, sterile water for injection). Calcium chloride 1.8 ml was added to give a final ionized calcium concentration of 1.25 mmol/L. This solution was used for both dialysate and for infusate (intravenous replacement solution). Ultrafiltration was set at net 300 cc per hour. Over the course of four days the patient remained on this form of dialysis with no complications. His creatinine fell quickly on dialysis indicating excellent dialysis adequacy and by the fourth day of dialysis was down almost to the normal level. His bicarbonate level remained between 21 and 24 mmol/L throughout, and his lactate level, which had been 1.6 mmol/L, fell to 0.9. The patient's condition improved dramatically and dialysis was stopped. He continued to improve and was able to be discharged home on day 18.

c) A 24-year old male developed acute renal failure after a prolonged intensive care admission from motor vehicle trauma. He developed severe metabolic acidosis requiring regular infusion of intravenous bicarbonate. As well, he required total parenteral nutrition and had high glucose levels. He was started on continuous veno venous hemodialysis with the Prisma dialysis machine and the concentrate 1L/hour, as described above used for dialysate. He did not require hemofiltration. Calcium was replaced intravenously, at 1.4 mmol/hour when his serum calcium dropped below the lower threshold of normal (2.2 mmol/L). His blood sugar remained in the high normal range but did not become excessively hyperglycemic and never hypoglycemic. He received this form of dialysis for over 28 days before he could be switched to peritoneal dialysis and transferred from the intensive care unit.

d) A 78 year old woman with a history of type 2 diabetes mellitus on the oral hypoglycemic agent Metformin 500 mg three times daily developed acute renal failure. She had a profound metabolic acidosis with pH was 7.19, $pCO_2$ 19, and serum bicarbonate 9. She was started on urgent continuous veno venous haemodialysis hemofiltration via an internal jugular catheter. She was initially started on Hemosol a low glucose containing (5 mmol/L) lactate buffered dialysate (40 mmol/L) (Hospal Gambro Lundia, Sweden) as dialysate running at one litre per hour. Ultrafiltration replacement with Hemosol was set at one liter per hour. Six hours after starting this regimen the patients acid base status was found to have deteriorated with the bicarbonate level down to 5 mmol/L and the blood gases also deteriorating to pH 6.99, $pO_2$ 136, $pO_2$ 8, bicarbonate was 2 on blood gasses. A bicarbonate drip was started with three ampules of bicarbonate in normal saline at 200 cc per hour. The lactate level was found to be 21.2 mmol/L and it had been 12.9 on admission. The lactate buffered hemosol was discontinued as both infusate and dialysate and switched over to the dialysate as described in Example 1 a bicarbonate infusate. Over the course of the next four hours, her bicarbonate level rose to 19 mmol/L then to 27 after 12 hours. Her lactate level dropped to 6 then to 0.9 within 12 hours. Over the course of 12 hours of dialysis with the bicarbonate infusate as described above, her urine output, which had been less than 30 cc per hour, increased to 100 cc per hour. She did not require further dialysis after this point. Her condition improved on antibiotic therapy and she was able to be discharged home on day 8.

e) A 54 year old man with a history of type 2 diabetes was treated for acute renal failure developing after therapy for cellulitis and sepsis. He had also required multiple operative procedures for debridement. At the time he was started on dialysis, he was hypotensive and had an acidosis. He was initially started on Hemosol dialysate at 1 liter per hour and as an infusate at 1 liter per hour. Net UF was set at 200 cc per hour. He became hypotensive on the following day when his lactate level was found to be 8 mmol/L. He required large doses of inotropic solutions and bicarbonate infusion. He was switched to dialysate prepared by the concentrate as above using intravenous bicarbonate solution as replacement and intravenous calcium as above when needed. On this aggressive bicarbonate replacement his bicarbonate increased to normal 25 mmol/L and his sodium remained at 140. Despite aggressive therapy and continuing CVVHD the patient succumbed after 6 days although with a normal bicarbonate level.

Example 3

Intensive care patients dialysed with the solution of the invention a) Thirty patients were dialyzed using the concentrate as described above from January 1996 to Oct. 20, 1997 on compassionate use clinical trial, mostly at 1 to 2 L/hour as dialysate. The survival was 65% to leaving the intensive care unit.

b) In a further clinical trial, 25 patients at three dialysis centers in Toronto Ontario, Canada, were randomized to 48 hours of low glucose Dianeal (lactate buffered) or the concentrate prepared in Example 1 for 48 hours in random order. In 12 patients receiving the bicarbonate dialysate for the first 48 hours of dialysis the results are summarized in Table 1.

The other 13 patients received 48 hours of dianeal followed by 48 hours of bicarbonate dialysate as made from concentrate described above. The results are summarized in Table 2.

Survival was similar in both groups and average 55% in leaving the intensive care unit, but only 35% in leaving hospital, typical of many reported survival numbers. Dialysis efficacy was equal in both groups.

In summary, the invention has been used in over 50 patients with as good or better metabolic control than lactate buffered dialysis solutions. Patients with acute renal failure, requiring slow methods of dialysis are a very ill group of patients with high mortality. Use of the bicarbonate dialysate embodied in the invention as described above provides good metabolic control in addition to effective use as a dialysate or intravenous replacement solution.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

TABLE 1

|  | Baseline Mmol/L | 48 hours of Dianeal Mmol/L | 48 hours of Bicarbonate Dialysate Mmol/L |
|---|---|---|---|
| HCO3 | 20.9 | 23.9 | 25.7 |
| Lactate | 1.9 | 1.72 | 2.36 |
| Glucose | 8.8 | 10.7 | 12.0 |

TABLE 2

|  | Baseline Mmol/L | 48 hours of Dianeal Mmol/L | 48 hours of Bicarbonate Dialysate Mmol/L |
|---|---|---|---|
| HCO3 | 13.9 | 22.0 | 25.0 |
| Lactate | 2.6 | 2.4 | 1.5 |
| Glucose | 9.3 | 10.1 | 8.7 |

We claim:

1. A method for providing continuous renal replacement therapy to a patient comprising administering a calcium-free sterile dialysis solution comprising Na 140±14 mmol/l, Mg 0.75±0.07 mmol/l, Cl 106.5±10 mmol/l, and HCO3 35.0±3.5 mmol/l to a patient in need thereof.

2. A method for providing peritoneal dialysis to a patient comprising administering a calcium-free sterile dialysis solution comprising Na 140±14 mmol/l, Mg 0.75±0.07 mmol/l, Cl 106.5±10 mmol/l, and HCO3 35.0±3.5 mmol/l to a patient in need thereof.

3. A method according to claim 2 wherein the dialysis solution further comprises dextrose in a concentration of 2.5% w/v.

4. A method of reducing potassium levels and fluid volume during cardiopulmonary bypass surgery comprising administering a calcium-free sterile dialysis solution comprising Na 140±14 mmol/l, Mg 0.75±0.07 mmol/l, Cl 106.5±10 mmol/l, and HCO3 35.0±3.5 mmol/l to a patient in need thereof.

5. A method for hemofiltration comprising administering a calcium-free sterile infusate comprising Na 140±14 mmol/l Mg 0.75±0.07 mmol/l, Cl 106.5±10 mmol/l, and HCO3 35.0±3.5 mmol/l to a patient in need thereof.

6. A method of treating dysentery comprising administering a calcium-free sterile solution comprising 90 mMol/l sodium; 68.5 mMol/l chloride; 22 mMol/l bicarbonate; and 277 mMol/l glucose to a person in need thereof.

7. A kit for preparing a dialysis solution comprising (a) one 80 ml unit of a calcium-free concentrate comprising sodium chloride (NaCl) 86.87±8.6 g/l, magnesium chloride ($MgCl_2$) 2.05±0.2 g/l, and sodium bicarbonate ($NaHCO_3$) 39.69±3.9 g/l and (b) one litre of sterile water.

8. A kit for preparing a dialysis solution according to claim 7 further comprising (c) one litre of a 5% w/v dextrose solution in water and (d) a second 80 ml unit of a concentrate comprising sodium chloride (NaCl) 86.87±8.6 g/l, magnesium chloride ($MgCl_2$) 2.05±0.2 g/l, and sodium bicarbonate $NaHCO_3$) 39.69±3.9 g/l.

9. A method of preparing a sterile dialysis solution comprising diluting a sterile, calcium free bicarbonate dialysis concentrate comprising sodium chloride (NaCl) 86.87±8.6 g/l, magnesium chloride ($MgCl_2$) 2.05±0.2 g/l, and sodium bicarbonate ($NaHCO_3$) 39.69±3.9 g/l in a sufficient amount of water to prepare a dialysis solution comprising Na 140±14 mmol/l, Mg 0.75±0.07 mmol/l, Cl 106.5±10 mmol/l, and HCO3 35.0±3.5 mmol/l.

10. A method for providing continuous renal replacement therapy to a patient in need thereof comprising administering a sterile dialysis solution prepared according to the method of claim 9 to a patient in need thereof.

11. A method for providing peritoneal dialysis to a patient comprising administering a sterile dialysis solution prepared according to the method of claim 9 to a patient in need thereof.

12. A method of reducing potassium levels and fluid volume during cardiopulmonary bypass surgery comprising administering a sterile dialysis solution prepared according to the method of claim 9 to a patient in need thereof.

13. A method for treating acute renal failure in a critically ill patient without introducing calcium into the blood removed from the patient during dialysis comprising administering a sterile dialysis solution prepared according to the method of claim 9 to a patient in need thereof.

14. A method for treating acute renal failure in a critically ill patient without introducing calcium into the blood removed from the patient during dialysis comprising administering a calcium-free sterile dialysis solution comprising Na 140±14 mmol/l, Mg 0.75±0.07 mmol/l, Cl 106.5±10 mmol/l, and HCO3 35.0±3.5 mmol/l to a patient in need thereof.

15. A method according to claim 10 wherein the patient is a liver transplantation patient.

16. A method of preparing a sterile infusate comprising diluting a sterile, calcium free bicarbonate concentrate comprising sodium chloride (NaCl) 86.87±8.6 g/l, magnesium chloride ($MgCl_2$) 2.05±0.2 g/l, and sodium bicarbonate ($NaHCO_3$) 39.69±3.9 g/l in a sufficient amount of water to prepare an infusate comprising Na 140±14 mmol/l, Mg 0.75±0.07 mmol/l, Cl 106.5±10 mmol/l, and HCO3 35.0±3.5 mmol/l.

17. A method for providing hemofiltration to a patient comprising administering a sterile infusate prepared according to the method of claim 16 to a patient in need thereof.

18. A method of preparing a sterile oral electrolyte solution for fluid replacement comprising diluting a sterile, calcium free bicarbonate concentrate comprising sodium chloride (NaCl) 86.87±8.6 g/l, magnesium chloride ($MgCl_2$) 2.05 ±0.2 g/l, and sodium bicarbonate ($NaHCO_3$) 39.69±3.9 g/l in a sufficient amount of water to prepare an electrolyte solution comprising Na 140±14 mmol/l, Mg 0.75±0.07 mmol/l, Cl 106.5±10 mmol/l, and HCO3 35.0±3.5 mmol/l.

\* \* \* \* \*